United States Patent [19]

Mascioli et al.

[11] Patent Number: 4,752,618
[45] Date of Patent: Jun. 21, 1988

[54] METHOD OF MINIMIZING EFECTS OF INFECTION THROUGH DIET

[75] Inventors: Edward A. Mascioli, Cambridge; George L. Blackburn, Jamaica Plain; Bruce R. Bistrian, Ipswitch; Vigen K. Babayan, Waban, all of Mass.

[73] Assignee: New England Deaconess Hospital, Boston, Mass.

[21] Appl. No.: 630,732

[22] Filed: Jul. 12, 1984

[51] Int. Cl.$^4$ ............................................ A61K 31/335
[52] U.S. Cl. .................................... 514/549; 514/552; 514/560
[58] Field of Search ..................... 514/549, 552, 560

[56] References Cited

U.S. PATENT DOCUMENTS 4,678,808  7/1987  Ward et al. ..................... 514/560

FOREIGN PATENT DOCUMENTS 2139889A  11/1984  United Kingdom .

OTHER PUBLICATIONS

Black et al, "Eicosapentaenoic Acid: Effect on Brain Prostaglandins, Cerebral Blood Flow and Edema in Ischemic Gerbils, vol. 15, No. 1, Jan.-Feb. 1984, pp. 65-69, Stroke.
Sanders et al, "Effect on Blood Lipids and Haemostasis of a Supplement of Cod-Liver Oil, Rich in Eicosapentaenoic and Docosahexaenoic Acids, in Healthy Young Men", Clin Sci., vol. 61, 1981, pp. 317-324.
Cook et al., "Elevated Thromboxane Levels in the Rat During Endotoxic Shock", J. Clin. Invest., vol. 65, Jan. 1980, pp. 227-230.
Dyerberg et al, "Eicosapentaenoic Acid and Prevention of Thrombosis and Atherosclerosis", The Lancet, Jul. 15, 1978, pp. 117-119.
Dyerberg et al, "The American Journal of Clinical Nutrition", 28: Sep. 1975, pp. 958-966-Fatty Acid Composition of the Plasma Lipids in Greenland Eskimos.
Culp et al.-"The Effect of Dietary Supplementation of Fish Oil on Experimental Myocardial Infarction, Prostaglandins-1980, vol. 20, No. 6, pp. 1021-1031.
Angela et al-Chem. Abst. vol. 52 (1958), p. 18923C.
Boyd et al-Chem. Abst., vol. 70 (1969), p. 26826U.
Teige et al-Chem. Abst., vol. 89 (1978), p. 4964C.
Osol et al-The Dispensatory of the U.S. 25th edit. (1955), pp. 346-347.
Martindale-The Extra Pharmacopoeia, vol. 1 (23rd edit) (1952), pp. 771-772.
Black et al-Chem. Abst., vol. 94 (1981), p. 29201t.

*Primary Examiner*—Sam Rosen
*Attorney, Agent, or Firm*—Lahive & Cockfield

[57] ABSTRACT

Disclosed is a method of minimizing infection and minimizing the risks of infection in at risk animals and patients. A dietary supplement to accomplish this objective is also disclosed. The method includes the step of administering a diet rich in $\omega$3 fatty acids, for example by adding a substantial proportion of fish oils to the diet. The dietary supplement is particularly well suited to patients receiving total parenteral nutrition.

22 Claims, No Drawings

METHOD OF MINIMIZING EFECTS OF INFECTION THROUGH DIET

ACKNOWLEDGEMENT

Funding for the research which led to this application was furnished, in part, by grant GM-30632 from the Institute of General Medical Sciences, National Institutes of Health.

BACKGROUND OF THE INVENTION

The present invention relates to a method of dietary control which reduces the effects of infection as well as minimizing the effects of subsequent infection in at risk animals, particularly human patients. A dietary supplement useful in the method of the invention is also disclosed.

Animals can be infected by many agents which break down the natural defenses and cause illness. These agents include bacteria, viruses, parasites, and fungi. While a great number of drugs have been developed to combat these infectious agents, the primary defense is the body's own immune system. The effectiveness of the body's defensive system against infection depends on the level of certain chemicals, e.g., prostaglandins, in the blood and cell membranes. These chemicals are synthesized from precursor molecules, e.g., fatty acids, obtained in the diet. In fact, some antiinfection drugs work by modifying the levels of synthesis of these molecules.

The amount and family of fatty acids in the diet is one of the keys to nutrition. There are three major families of polyunsaturated fatty acids: $\omega 3$, $\omega 6$ and $\omega 9$. The names are based on the location of the closest double bond to the methyl end of the fatty acid; that is, if the closest double bond is between the third and fourth carbon atoms from the methyl group, the molecule is a $\omega 3$ fatty acid while if the double bond is between the sixth and seventh carbons, it is classified as a $\omega 6$ fatty acid. Mammals can desaturate or elongate fatty acid chains but cannot interconvert fatty acids from one family to another. The most significant fatty acids are those which have been desaturated and elongated to the twenty carbon length. The $\omega 9$ fatty acids are elongated to form eicosatrienoic acids ($C20:3\omega 9$), the $\omega 6$ fatty acids form arachidonic acid ($C20:4\omega 6$), and the $\omega 3$ fatty acids form eicosapentaenoic acid ($C20:5\omega 3$) or docosahexaenoic acid ($C22:6\omega 3$). The notation ($Chd\!-\!:\!\_\omega\_$) gives the number of carbons in the chain, the number of double bonds and the class of the fatty acid, respectively.

Most people in industrialized nations obtain a high proportion of their fatty acids from meat fats and vegetable oils. These fatty acid sources are high in $\omega 6$ fatty acids and low in $\omega 3$ fatty acids. Therefore, arachidonic acid is the predominant twenty carbon desaturated and elongated fatty acid in the plasma and membranes of these people. In countries where fish oil, which contains a high proportion of $\omega 3$ fatty acids, is the predominant fatty acid source, eicosapentaenoic acid is the major desaturated fatty acid found in the plasma and membranes.

Part of the significance of the twenty carbon fatty acids is their ability to act as substrates in the prostanoid synthesis pathway which forms prostaglandins from fatty acids. The first enzyme in this pathway is cyclo-oxygenase whose primary substrate in mammals is arachidonic acid. In the platelets, arachidonic acid is modified by the enzymes of the pathway to form thromboxane $A_2$, a potent platelet aggregator and vasoconstrictor. In endothelial cells, arachidonic acid forms prostacyclin $I_2$, a vasodilator and platelet antiaggregator. Both thromboxane $A_2$ and prostacyclin $I_2$ are prostaglandins of the "2" series.

However, the enzyme cyclo-oxygenase can also use eicosapentaenoic acid as a substrate. In the platelets, eicosapentaenoic acid is formed into thromboxane $A_3$. Thromboxane $A_3$ is a weak vasoconstrictor but unlike thromboxane $A_2$, it will not aggregate platelets. In endothelial cells, prostacylin $I_3$, which has vasodilatory and platelet antiaggregating properties similar to prostacyclin $I_2$, is formed from eicosapentaenoic acid. Thromboxane $A_3$ and prostacyclin $I_2$ are prostaglandins of the "3" series. If docosahexaenoic acid is formed upon chain elongation and desaturation, or since it is present in fish oils, it also can be used as a substrate for cyclo-oxygenase. This also decreases the level of series "2" prostaglandin formation.

The fact that both $\omega 3$ and $\omega 6$ fatty acids can act as substrates for the prostanoid synthesis pathway led to the theory that dietary manipulation could modify the levels of type 2 and type 3 prostaglandins in the platelets and cell membranes. According to this theory, the availability of $\omega 3$ fatty acids in the diet would cause a decrease in the level of type 2 prostaglandins in the plasma and membranes through competitive inhibition for the enzymes which normally use $\omega 6$ fatty acids as substrates. In one experiment on dietary manipulation, Sanders, Vickers and Haines, *Clin. Sci.* 61:317-324 (1981), investigated the effect on blood lipids and hemostasis in healthy young men by supplementing their diet with cod liver oil, an oil rich in $\omega 3$ fatty acids. These researchers found that the ratio of $\omega 3$ to $\omega 6$ fatty acids and resulting products was increased in the platelets and erythrocyte phosphoglycerides by this diet modification.

In a series of papers by Dyerberg et al, e.g., *Am. J. Clin. Nutr.* 28:958-966 (1975), *Lancet* 2:433-435 (1979), and *Am. J. Clin. Nutr.* 33:2657-2661 (1970), the effects of diet high in $\omega 3$ fatty acids on heart disease were studied. The Greenland Eskimos, who have a low meat and high fish oil diet, were the test subjects. Since meat is high in $\omega 6$ fatty acids while fish oils have significant quantities of $\omega 3$ fatty acids, these studies provided a comparison between high $\omega 6$ and high $\omega 3$ diets. The Eskimos with the high $\omega 3$ fatty acid diets had significantly lower incidence of heart disease than Eskimos who had high $\omega 6$ fatty acid diets. The latter group were primarily Eskimos who had moved to Denmark and changed their diet to have a substantial proportion of $\omega 6$ fatty acids. These experiments showed that dietary manipulation could change the susceptibility to heart disease.

Some hospitalized patients, particularly critically ill patients, receive total parenteral nutrition. Since most patients receiving parenteral nutritional systems have a high risk of infection, a diet which minimizes the risk of infection would be a substantial benefit to this class of patients. Parenteral nutrition diets include a source of fatty acids since fatty acids are necessary for adequate biochemical functioning. However, standard parenteral diets use fatty acids derived primarily from soybean or safflower oil which as with most plant oils, are high in $\omega 6$ fatty acids but have little or no $\omega 3$ fatty acid content. While some $\omega 6$ fatty acids are essential to good health, somewhere between 2 and 4 percent of the total calorie content is all that is necessary. Conventional parenteral nutrition diets supply 10–15 percent, occasionally as high as 50 percent, of the calorie content as the $\omega 6$ fatty acids, a clear excess.

Lowering $\omega 6$ fatty acids may lead to an increase in platelet thromboxane $A_3$ levels. One theory for the decreased heart disease among eskimoes is that the platelets are not as "sticky" if the thromboxane $A_2$ levels are lowered. Since the production of thromboxane $A_3$ is normally at the expense of thromboxane $A_2$, a diet which lowers the $\omega 6$ fatty acid levels might lead to a decrease in heart disease.

Cook, Wise and Halushka, J. Clin. Invest. 65:227 (1980) investigated the thromboxane $A_2$ levels in rats challenged with endotoxin. They found endotoxin shock increases thromboxane $A_2$ levels in the platelets. Rats treated with imidazole (a thromboxane synthetase inhibitor), indomethacin (a fatty acid cyclo-oxygenase inhibitor), or those animals with essential fatty acid deficiency ($\omega 6$ fatty acid deficiency) had higher survival rates to endotoxin shock than did normal rats. All of the groups of animals with higher survival rates exhibited lower thromboxane $A_2$ levels.

Accordingly, an object of the invention is to provide a method of minimizing the effects of infection and minimizing the effects of subsequent infection in at risk animals, particularly humans, by administering a diet which promotes resistance to infection without interfering with essential bodily processes. Another object of the invention is to provide a dietary supplement which provides sufficient nutrition in animals while reducing the risk of infection. A further object of the invention is to provide a method of treating patients, primarily patients having high risk of infection, with a dietary supplement which provides essential fatty acids while assisting in resistance to infection. These and other objects and features of the invention will be apparent from the following description.

SUMMARY OF THE INVENTION

The present invention features a method of minimizing the effects of infection and minimizing the effects of subsequent infection in at risk animals. The invention includes the step of administering a diet rich in $\omega 3$ fatty acids, preferably by administration of oils rich in $\omega 3$ fatty acids. Oils rich in $\omega 3$ fatty acids are selected from a group consisting of fish oils, e.g., herring, anchovy, cod, and menhaden oil, and various unusual plant oils. The oils may be concentrated to provide a high percentage of $\omega 3$ fatty acids per unit volume. The preferred animals for administration of the diet are humans, e.g., hospitalized patients. The patients may have an infection at the time of administration of the diet or may be members of a class having a high risk of infection. These high risk patients include those suffering with secondary immunosuppression due to chemotherapy or diabetes mellitus, protein-malnourished patients, or patients undergoing abdominal surgery. The infections may be wound infections, empyemas, bacteremias, abscesses, or septicemias. These infections are caused by a variety of infectious agents including bacteria, viruses, parasites, and fungi. The oils rich in $\omega 3$ fatty acids may be administered orally or intravenously.

The invention also features a dietary supplement having 10 to 20 percent by weight of an oily fraction rich in $\omega 3$ fatty acids, 1–2 percent by weight of an emulsifier and sterile water. The emulsifier is selected from a group consisting of egg yolk phospholipids and soybean phospholipids. The dietary supplement may also include 1–3 percent of an osmolality modifier such as glycerin. The oily fraction consists of a mixture of oils rich in $\omega 3$ fatty acids and oils rich in $\omega 6$ fatty acids, e.g., oils rich in linoleic acid. The oils rich in $\omega 3$ fatty acids provide 10–90 percent of the total fatty acids. Oils rich in $\omega 6$ fatty acids include safflower, sunflower, and soybean oils while oils rich in $\omega 3$ fatty acids include fish oils derived from herring, cod, anchovy and menhaden as well as unusual plant oils.

The invention further features a method of minimizing the effects of infection and minimizing the effects of subsequent infection in at risk patients by administration of a dietary supplement. This supplement supplies all the essential fatty acids while providing resistance to infection by modification of the substrates for some enzyme processes. The dietary supplement of the invention is useful in this method.

DESCRIPTION

The present invention relates to a method of using dietary control to minimize infection and to minimize the risk of subsequent infection in high risk animals and patients. Mixtures of lipid-containing oils replace the standard fatty acid portion of conventional dietary supplements, e.9., those used in parenteral feedings. By substituting $\omega 3$ fatty acids for conventional $\omega 6$ fatty acids, survival to challenge with infection is improved.

Conventional dietary supplements have primarily soybean or safflower oil as their lipid or fatty acid source. Soybean oil has approximately 53 percent $\omega 6$ fatty acids and only 8 percent $\omega 3$ fatty acids while safflower oil has almost 78 percent $\omega 6$ fatty acids and substantially no $\omega 3$ fatty acids. In contrast, fish oils such as menhaden oil have 22 percent or more $\omega 3$ fatty acids and only 2–5 percent $\omega 6$ fatty acids. By replacing the predominantly $\omega 6$ fatty acid-containing oils with $\omega 3$ fatty acid-containing oils, the levels of type 2 prostaglandins is reduced and the levels of type 3 prostaglandins increased. Since infectious agents such as endotoxins increase the levels of type 2 prostaglandins, the lowering of type 2 prostaglandins by diet may improve chance of survival after challenge with these infections. For example, patients receiving parenteral dietary nutrition normally have lowered resistance due to immunosuppression. Infection is one of the major causes of complication, including death, in this type of patient. By dietary modifications, survival and full recovery are promoted.

The following non-limiting examples will show the efficacy of the present invention.

EXAMPLE 1

This Example illustrates that animals fed a diet in which the primary lipid source are oils rich in $\omega 3$ fatty acids rather than a diet containing oils rich in $\omega 6$ fatty acids promotes survival when the animals are challenged with endotoxin. The animals were healthy, male Hartley strain guinea pigs from Elm Hill Breeding Laboratories in Chelmsford, Mass. The weight of the animals at the initiation of the experiment were 200 to 250 grams. The animals were initially fed standard laboratory guinea pig chow made by Ralston-Purina Company for one week and then switched to the experimental diets.

Table 1 lists the ingredients of the diets used for both groups of guinea pigs.

TABLE 1
DIET COMPOSITION: MODIFIED REID-BRIGGS SEMI-PURIFIED GUINEA PIG DIET

| INGREDIENT | AMOUNT PER KILOGRAM (GRAMS) |
|---|---|
| Casein | 300 |
| Corn Starch | 200 |
| Sucrose | 89 |
| Glucose | 0 |
| Cellulose | 150 |
| Oil | 150 |
| Arginine | 3 |
| Salt Mix | 90 |
| Vitamin Mix | 10 |
| Choline Chloride | 4 |
| Ascorbic Acid | 4 |
| | 1000 gm total |

The diets fed to the two groups of guinea pigs were identical except the control group received 150 gm of safflower oil while the second group received 145 gm of menhaden with 5 gm of safflower oil added to prevent linoleic acid deficiency. The diets are standard Reid-Briggs guinea pig diets except the oil content is raised so the diet contains 15 percent by weight of lipid as opposed to traditional 7.3 percent. This allows 36 percent of the dietary calories to be lipid-derived as compared wit the the standard 15 percent. Table 2 illusrates the lipid content of safflower oil and menhaden oil.

TABLE 2
DIETARY OIL FATTY ACID COMPOSITION (IN PERCENT TOTAL FATTY ACIDS)

| FATTY ACID | SAFFLOWER OIL | MENHADEN OIL |
|---|---|---|
| C14:0 Myristic | .1 | 11.6 |
| C16:0 Palmitic | 6.5 | 13 |
| C16:1ω7 Palmitoleic | | 13.3 |
| C18:0 Stearic | 2.4 | 2.1 |
| C18:1ω9 Oleic | 13.1 | 6.7 |
| C18:1ω7 | | 3.3 |
| C18:2ω6 Linoleic | 77.7 | 1.1 |
| C20:4ω6 Arachidonic | | .7 |
| C20:4ω3 | | 1.9 |
| C20:5ω3 Eicosapentaenoic | | 17.3 |
| C22:5ω6 | | .4 |
| C22:5ω3 | | 2.0 |
| C22:6ω3 | | 8.2 |
| C24:1ω9 | | .4 |
| Other | .2 | 18 |

The animals were kept on these diets for six weeks prior to endotoxin challenge. Each of the groups were subdivided into two groups at 6 weeks and one of the subgroups received 1 cc of a 0.9 percent saline solution while the other half received 10 mg/kg body weight of the drug ibuprofen intra-peritoneally. Ibuprofen is a cyclo-oxygenase inhibitor. One hour after administration of the saline or ibuprofen, the animals all received 0.5 mg/100 gm body weight of the endotoxin, an approximate $LD_{50}$ dosage for these animals. The endotoxin, a lipopolysaccharide derived from E. coli, was obtained from Difco Laboratories. A portion of the animals was retained for four days to determine survival against endotoxin while another portion were sacrificed one hour after endotoxin administration for collection of plasma. The sacrificed animals were decapitated and the blood collected in EDTA tubes to which 25 mcg/cc ibuprofen had been added. The blood was spun down, the plasma separated and frozen for subsequent fatty acid, thromboxane $B_2$, and 6-keto-PGF$_1$ © analysis.

One problem with this diet rich in ω3 fatty acids was that over the six weeks of the experiment, the control group (ω6 fatty acid rich diet) guinea pigs gained an average of 304 gms while the guinea pigs on the ω3 fatty acids rich diet gained an average of only 113 grams. By increasing the ω6 fatty acids from 2 percent to 4 percent of the total intake, this weight gain differential might be obviated.

Table 3 illustrates the survival of the two groups of uinea pigs at 12, 24, 48, and 72 hours after endotoxin challenge. While both groups show substantially equal survival at 12 hours, from 24 hours on the group fed the diet rich in ω3 fatty acids (menhaden oil) showed a threefold increase in survival.

TABLE 3
SURVIVAL FROM $LD_{50}$ ENDOTOXIN

| DIET | 12 HOURS n percent | 24 HOURS n percent | 48 HOURS n percent | 72 HOURS n percent |
|---|---|---|---|---|
| Safflower Oil (n = 30) | 16 (53) | 6 (20) | 4 (13) | 4 (13) |
| Menhaden Oil (n = 30) | 20 (67) | 18 (60) | 15 (50) | 14 (47) |

Clearly, replacing the ω6 fatty acids by ω3 fatty acids enhances survival to endotoxin shock.

Table 4 illustrates the levels of thromboxane in the $B_2$ plasma of the two groups. Thromboxane $B_2$ is a stable metabolite of thromboxane $A_2$ so it was used for the measurement because of the rapid metabolization of the thromboxane $A_2$. While it is evident from Table 4 that ibuprofen and endotoxin challenge clearly affect the thromboxane $B_2$ level, it is not clear that the diet affects the thromboxane $B_2$ level.

TABLE 4
PLASMA THROMBOXANE $B_2$ LEVELS

| DIET | IBUPROFEN | BEFORE | AFTER |
|---|---|---|---|
| Safflower Oil | no | 172 ± 26 | 451 ± 103 |
| Safflower Oil | yes | 64 ± 9 | 78 ± 13 |
| Menhaden Oil | no | 292 ± 60 | 397 ± 25 |
| Menhaden Oil | yes | 98 ± 28 | 211 ± 50 |

X ± SEM in pg/ml
N = 6 for all groups

Several explanations of these results are possible. One possibility is that survival cannot be correlated to thromboxane $A_2$ or $B_2$ levels. Second, the testing for thromboxane $B_2$ itself may cause an artifact. Measurements were made by a radioimmunoassay procedure and no studies have been done to differentiate between thromboxane $B_2$ and thromboxane $B_3$, the stable metabolite of thromboxane $A_3$. Since there is only a small structural difference between these type 2 and type 3 thromboxanes (one double bond), it is possible that there is significant cross reactivity between the thromboxanes so part of the measured thromboxane $B_2$ could actually be thromboxane $B_3$. Thromboxane $A_3$ should be produced from the ω3 fatty acids.

Table 5 shows the plasma 6-keto-PGF$_1$ α levels for the various groups. 6-keto-PGF$_1$ is a stable metabolite of prostacyclin $I_2$.

TABLE 5
PLASMA 6-KETO-PGF$_1$ α LEVELS

| DIET | IBUPROFEN | ENDOTOXIN BEFORE | ENDOTOXIN AFTER |
|---|---|---|---|
| Safflower Oil | no | 43.7 ± 11.3 | 544 ± 179 |
| Safflower Oil | yes | 58.3 ± 14.0 | 71.6 ± 10.4 |
| Menhaden Oil | no | 81.0 ± 10.7 | 502 ± 167 |

TABLE 5-continued

| | | PLASMA 6-KETO-PGF$_1$ α LEVELS | |
|---|---|---|---|
| | | | ENDOTOXIN |
| DIET | IBUPROFEN | BEFORE | AFTER |
| Menhaden Oil | yes | 55.7 ± 13.5 | 138.3 ± 39.7 |

X ± SEM in pg/ml
n = 6 for all groups

As with the thromboxane B$_2$ assay, cross reactivity with Δ17-6keto -PGF$_1$ α, the stable tabolite of prostacyclin I$_3$, was not tested. This may account for the lack of a difference in the 6-keto-PGF$_1$ α levels among the groups. Δ 17-6 keto-PGF$_1$ α is produced from ω3 fatty acids.

What is evident from this experiment is that the diet modification promoted enhanced survival of the guinea pigs fed the diet rich in ω3 fatty acids. The mechanism for enhanced survival is not clear, however.

EXAMPLE 2

This Example illustrates one procedure for forming a dietary supplement for patients which will enhance resistance to infection. Patients who may benefit from such a supplement include those with secondary immunosuppression due to diabetes mellitus or chemotherapy. In these latter patients, the total polymorphonuclear leukocyte count is normally less than 1,000/mm$^3$. Another group of patients who could benefit are protein-malnourished patients. In these patients, the serum albumin level in plasma is normally less than 3.2 gm/dl or recent weight loss of greater than 10 percent of original body weight has occurred.

The oil emulsion is made as follows. For each liter of emulsion, 100-200 gm of refined and bleached oil rich in ω3 fatty acids is mixed with 11 gms of an emulsifier, e.g., egg yolk phospholipids USP, 22.5 gms. of an osmolality modifier, e.g. glycerin USP, and sterile water USP to bring the volume to a liter. Specifically, the oil is added to a high shear mixer such as a Waring mixer with steel blades operated at 1,600 RPM. The phospholipids are added slowly to the oil and mixed at high speed for 6 minutes. Eight hundred milliliters of sterile water is added in a steady stream to the phospholipid and oil mixture and emulsified for 20 minutes at 1600 RPM. The attainment of the oil-in-water emulsion is confirmed by the "drop dispersion test." Emulsification is continued until the coarse oil emulsion disperses freely in water but not in oil.

The coarse emulsion is then passed through a high speed homogenizer five times until particle size is less than 1 micron. At that time, five more passes through the high speed homogenizer are performed and with each pass, glycerin is added to the emulsion. During the last five passes, additional water is added to make the final emulsion volume up to the one liter batch. Normally, all volumes are multiplied ten-fold and a ten liter batch is mixed at once.

Aliquots of the emulsion are set aside for measuring particle size which should be between 0.24 and 0.75 microns. The solutions are then passed through a five micron particle filter into sterile and pyrogen free evacuated containers. The emulsion is then sterilized at low temperature (105° C.) for 25 minutes. The solutions are cooled to room temperature and stored in the dark at 9° C. for one week. Prior to patient administration, the samples are retested for particle size and the presence of bacterial or endotoxin contamination. If the particle size is greater than 1 micron or the endotoxin concentration is greater than 1 ng, the batch of emulsion is discarded.

As previously noted, this dietary supplement can be used in patients who may be susceptible to a number of infectious agents. Examples of these infectious agents include E. coli, Pseudomonas, or Klebsiella for the gram negative bacteria, Staphylococcus aureus or albus for the gram positive bacteria, Herpes simplex or zoster for the viruses, and fungi such as Candida. A variety of parasites can also be controlled by this type of supplement.

While the method and dietary supplement disclosed herein will not necessarily prevent the onset of infection caused by these agents, it will promote survival of infected patients or animals. The specific method and dietary supplement set forth herein are purely illustrative and those skilled in the art may determine other modifications and variations of these procedures. Such other modifications and variations are included within the scope of the following claims.

What is claimed is:

1. A method of minimizing the effects of infection and minimizing the effects of subsequent infection in high risk patients comprising the steps of:
    administering to said patients a diet which is controlled in its caloric and fatty acid type intake, said diet containing 10-20 percent by weight of a mixture of fatty acid-containing oils, wherein said fatty acid-containing oils are selected from oils which have ω6 fatty acids as their primary fatty acids and oils which have ω3 fatty acids as their primary fatty acids, the oils having ω3 fatty acids as their primary fatty acids forming 10-90 percent of said mixture of fatty-acid-containing oils.

2. The method of claim 1 wherein said ω3 oils are selected from a group consisting of oils derived from herring, anchovy, and menhaden.

3. The method of claim 1 wherein said patients comprise patients who have an infection at time of administration of said diet.

4. The method of claim 3 wherein said patients are infected with infections selected from a group consisting of wound infections, empyemas, bacteremias, abscesses, and septicemias.

5. The method of claim 3 wherein said infections are caused by infectious agents selected from a group consisting of bacteria, viruses, parasites, and fungi.

6. The method of claim 3 wherein said humans comprise patients who have a high risk of infection at the time of administration of the diet.

7. The method of claim 6 wherein said patients at high risk of infection are selected from a group consisting of patients with secondary immunosuppression due to chemotherapy or diabetes mellitus, protein-malnourished patients, and patients undergoing abdominal surgery.

8. The method of claim 1 wherein said oils are administered orally.

9. The method of claim 1 wherein said oils are administered intravenously.

10. A method of minimizing the effects of infection and minimizing the effects of subsequent infection in high risk patients by administering a dietary supplement supplying essential fatty acids, said dietary supplement comprising:
    10-20 percent by weight of an oily fraction, said oily fraction containing a mixture of one or more oils which contain a greater percentage of $\omega$3 fatty acids than $\omega$6 fatty acids;

1-2 percent by weight of an emulsifier;

1-3 percent by weight of an osmoality modifier; and sterile water.

11. The method of claim 10 wherein said emulsifier is selected form a group consisting of egg yolks phospholipids and soybean phospholipids.

12. The method of claim 10 wherein said osmoality modifier comprises glycerin.

13. The method of claim 10 wherein said dietary supplement comprises a mixture of oils including oils which contain a greater percentage of $\omega$3 fatty acids than $\omega$6 fatty acids and oils rich in $\omega$6 fatty acids.

14. The method of claim 13 wherein said oils which contain greater percentage of $\omega$3 fatty acids that $\omega$6 fatty acids comprise 10–90 percent by weight of the total fatty acids in said supplement.

15. The method of claim 14 wherein said oils which contain a greater percentage of $\omega$3 fatty acids than $\omega$6 fatty acids comprise fish oils selected form a group consisting of oils derived from herring, anchovy and menhaden.

16. The method of claim 10 wherein said patients comprise patients who have an infection at time of administration of said dietary supplement.

17. The method of claim 16 wherein said patients are infected with infections selected from a group consisting of wound infection, empyemas, bacteremias, abscesses and septicemias.

18. The method of claim 16 wherein said infections are caused by infectious agents selected from a group consisting of bacteria, viruses, parasites and fungi.

19. The method of claim 16 wherein said patients comprise patients who have a high risk of infection at the time of administration of said dietary supplement.

20. The method of claim 16 wherein said patients having a high risk of infection are selected from a group consisting of patients with secondary immunosuppression due to chemoterapy or diabetes mellitus, protein-malnourished patients, and patients undergoing abdominal surgery.

21. The method of claim 10 wherein said dietary supplement is administered orally.

22. The method of claim 10 wherein said dietary supplement is administered intravenously.

* * * * *

UNITED STATES PATENT AND TRADEMARK OFFICE
CERTIFICATE OF CORRECTION

PATENT NO. : 4,752,618
DATED : June 21, 1988
INVENTOR(S) : Mascioli et al.

It is certified that error appears in the above-identified patent and that said Letters Patent is hereby corrected as shown below:

At Column 1, line 48 delete "(Chd__:__w__)" and insert --(C__:__w__)--.

At Column 4, line 27 delete "e.9." and insert --e.g.--.

At Column 5, line 26 delete "wit" and insert --with--.

At Column 5, line 66 delete "C" and insert --α--.

At Column 6, line 8 delete "uinea" and insert --guinea--.

At Column 5, line 26, delete "the" (second (occurrence)

At Column 2, line 12 delete "prostacylin" and insert --prostacyclin--.

Signed and Sealed this

Twenty-third Day of May, 1989

Attest:

DONALD J. QUIGG

*Attesting Officer*  *Commissioner of Patents and Trademarks*